US010856985B2

(12) United States Patent
Wei (10) Patent No.: US 10,856,985 B2
(45) Date of Patent: Dec. 8, 2020

(54) SYSTEM AND METHOD FOR ANNULOPLASTY

(71) Applicant: Abbott Cardiovascular Systems Inc., Santa Clara, CA (US)

(72) Inventor: Michael F. Wei, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 64 days.

(21) Appl. No.: 15/820,374

(22) Filed: Nov. 21, 2017

(65) Prior Publication Data
US 2019/0151089 A1 May 23, 2019

(51) Int. Cl.
*A61F 2/24* (2006.01)

(52) U.S. Cl.
CPC .......... *A61F 2/2451* (2013.01); *A61F 2/2466* (2013.01); *A61F 2210/0085* (2013.01); *A61F 2220/005* (2013.01); *A61F 2220/0008* (2013.01); *A61F 2220/0041* (2013.01); *A61F 2220/0091* (2013.01); *A61F 2250/0001* (2013.01); *A61F 2250/0007* (2013.01)

(58) Field of Classification Search
CPC ............ A61F 2/2442; A61F 2250/0007; A61F 2/2451; A61F 2220/005; A61F 2/2445; A61F 2/2448; A61F 2220/0008; A61F 2210/0085; A61F 2220/0091; A61F 2220/0041; A61F 2/2466; A61F 2250/0001; A61M 25/007; A61M 2025/0057
USPC ....................................... 604/537
See application file for complete search history.

(56) References Cited

U.S. PATENT DOCUMENTS

| 6,250,308 | B1 | 6/2001 | Cox |
| 7,241,310 | B2 | 7/2007 | Taylor et al. |
| 7,294,148 | B2 | 11/2007 | McCarthy |
| 7,438,711 | B2* | 10/2008 | Deniega ............ A61M 25/0043 604/523 |
| 7,500,989 | B2 | 3/2009 | Solem et al. |
| 7,758,639 | B2 | 7/2010 | Mathis |
| 7,828,843 | B2 | 11/2010 | Alferness et al. |
| 7,951,196 | B2 | 5/2011 | McCarthy |
| 8,523,940 | B2 | 9/2013 | Richardson et al. |
| 8,814,932 | B2 | 8/2014 | Edmunds |
| 2002/0173770 | A1* | 11/2002 | Flory ............... A61B 17/00491 604/537 |
| 2004/0133273 | A1* | 7/2004 | Cox ..................... A61F 2/2451 623/2.11 |

(Continued)

FOREIGN PATENT DOCUMENTS

EP 0775072 B1 * 11/1998 ........... B65D 1/0292

OTHER PUBLICATIONS

EP0775072B1—translation (Year: 1998).*

*Primary Examiner* — Brian A Dukert
*Assistant Examiner* — Rebecca Lynee Zimmerman
(74) *Attorney, Agent, or Firm* — Baker Botts L.L.P.

(57) ABSTRACT

A device for adjusting a shape of a coronary sinus in a heart of a patient, the device comprising a flexible tube having: an outer wall extending between a proximal end and a distal end; a first bore extending from the proximal end to the distal end; a proximal flange attached to the proximal end; a distal flange attached to the distal end; wherein, the outer wall includes at least one accordion-like hinge region.

18 Claims, 5 Drawing Sheets

(56) References Cited

U.S. PATENT DOCUMENTS

2012/0010694 A1* 1/2012 Lutter ................ A61F 2/2445
                                                               623/1.11
2016/0030175 A1* 2/2016 Madjarov ............ A61F 2/2445
                                                               623/2.37

* cited by examiner

SYSTEM AND METHOD FOR ANNULOPLASTY

BACKGROUND

In an effort to stem the risk of heart valve disease, various medical procedures have been developed to repair or replace poorly functioning or stenosed heart valves. In particular, annuloplasty procedures have been used to repair heart valves by way of open heart surgery or, on a more limited basis, by way of less invasive techniques.

Mitral regurgitation is a particular type of heart valve disease wherein the mitral valve fails to sufficiently close, and blood is allowed to backflow across the valve. Consequently, many mitral annuloplasty procedures are designed to make the mitral annulus smaller, particularly in the septal-lateral dimension, allowing the mitral valve leaflets to coapt more effectively and preventing mitral regurgitation.

In some instances, repair of the mitral valve involves placing an annuloplasty ring on the mitral valve. Certain procedures involve suture-based cinching to reshape the mitral valve. In addition, some percutaneous annuloplasty procedures involve placing a rigid structure in the coronary sinus, which is near but not exactly at, the actual location of the mitral annulus. Such procedures can be cumbersome and may not be particularly effective or safe in all patients due to the anatomy of the coronary sinus, the mitral annulus, and the nearby circumflex coronary artery. In particular, coronary sinus devices may not be as effective as surgically placed devices, and crossing of the coronary sinus over the circumflex artery can cause dangerous compression of the artery by an annular cinching device placed in the coronary sinus.

Heretofore, reliable anchoring of an annuloplasty ring at a desirable location has been difficult using percutaneous and less invasive techniques. In addition, some prior attempts have utilized rather stiff structures in order to obtain the required shape and support for the valve.

Consequently, there is a need for an annuloplasty procedure and device that overcomes the problems associated with prior approaches and devices.

SUMMARY OF THE INVENTION

In one embodiment, the invention is a device for adjusting a shape of a coronary sinus in a heart of a patient. In this embodiment, the device comprises a flexible tube having an outer wall extending between a proximal end and a distal end. A first bore extends from the proximal end to the distal end. A proximal flange is attached to the proximal end, and a distal flange is attached to the distal end. Under this configuration, the outer wall includes at least one accordion-like hinge region. The according like hinge region permits the outer wall to be shortened in axial length upon the application of an axial compression force. In some embodiments, the proximal flange defines a proximal opening, and an inner member passes slidingly through the proximal opening and extends to, and is connected to, the distal flange. Under this arrangement, the inner member defines a plurality of teeth on an external surface, the plurality of teeth configured to provide a ratchet control for passing slidingly through the proximal opening. In some embodiments, the inner member defines a second bore. In further embodiments, the outer wall defines at least one opening, thereby creating a passage between first bore and a space outside the flexible tube. Under this configuration, there is further provided at least one porous element attached to the outer wall, being shaped to cover the at least one opening. In some embodiments, the at least one porous element has an annular shape.

In another embodiment, the invention is a device for adjusting the shape of a coronary sinus, and in this embodiment the device comprises a flexible tube having an outer wall extending between a proximal end and a distal end. A first bore extends from the proximal end to the distal end. A proximal flange is attached to the proximal end, and a distal flange is attached to the distal end. Under this configuration, the first bore is filled with a fluid adhesive. In order to permit the fluid adhesive to pass from the first bore under pressure, the outer wall defines at least one opening, thereby creating a passage between first bore and a space outside the flexible tube. A porous element is attached to the outer wall, the porous element being shaped to cover the at least one opening. In some embodiments, the proximal flange defines a proximal opening, and an inner member passes slidingly through the proximal opening and extends to, and is connected to, the distal flange. Under this arrangement, the inner member defines a plurality of teeth which act as a ratchet for passing slidingly through the proximal opening, the proximal opening configured to act as a pawl for controlling the passage of the inner member through the proximal opening. In some embodiments, the inner member defines a second bore extending along an entire length of the inner member. In yet further embodiments, the porous element is shaped to have an annular shape.

In yet another embodiment, the invention is a method for adjusting the shape of a coronary sinus in a heart of a patient. The method comprises inserting a tube into a coronary sinus of the heart, wherein the tube has an elongate axis and an outer wall defining a bore, the outer wall further defining a plurality of openings. Further, a fluid adhesive is introduced into the bore. At an appropriate moment, a first amount of fluid adhesive is expelled from the bore through the plurality of openings and, thereby, the tube is allowed to become attached to an inner wall of the coronary sinus at a plurality of points adjacent the plurality of openings. When this stage is complete, the tube is shortened in the direction of the elongate axis, and thereby the coronary sinus is shortened. In some embodiments, the method further includes adding a curing agent into the bore, thereby causing the fluid adhesive in the bore to harden. In other embodiments, the method may further include introducing a source of ultraviolet light into the bore, thereby causing the fluid adhesive in the bore to harden. In other embodiments, the method may further include bending the tube, and bending the tube may include applying a longitudinal compression force to the tube in the direction of the elongate axis. In some embodiments, expelling an amount of fluid adhesive may include reducing a volume of the bore. In alternative embodiments, expelling a first amount of fluid adhesive includes adding a second amount of fluid adhesive into the bore.

These and other advantages of the invention may be understood when studied in light of the drawings, and the detailed description of some embodiments.

DETAILED DESCRIPTION OF THE PREFERRED EMBODIMENTS

Figure 1:
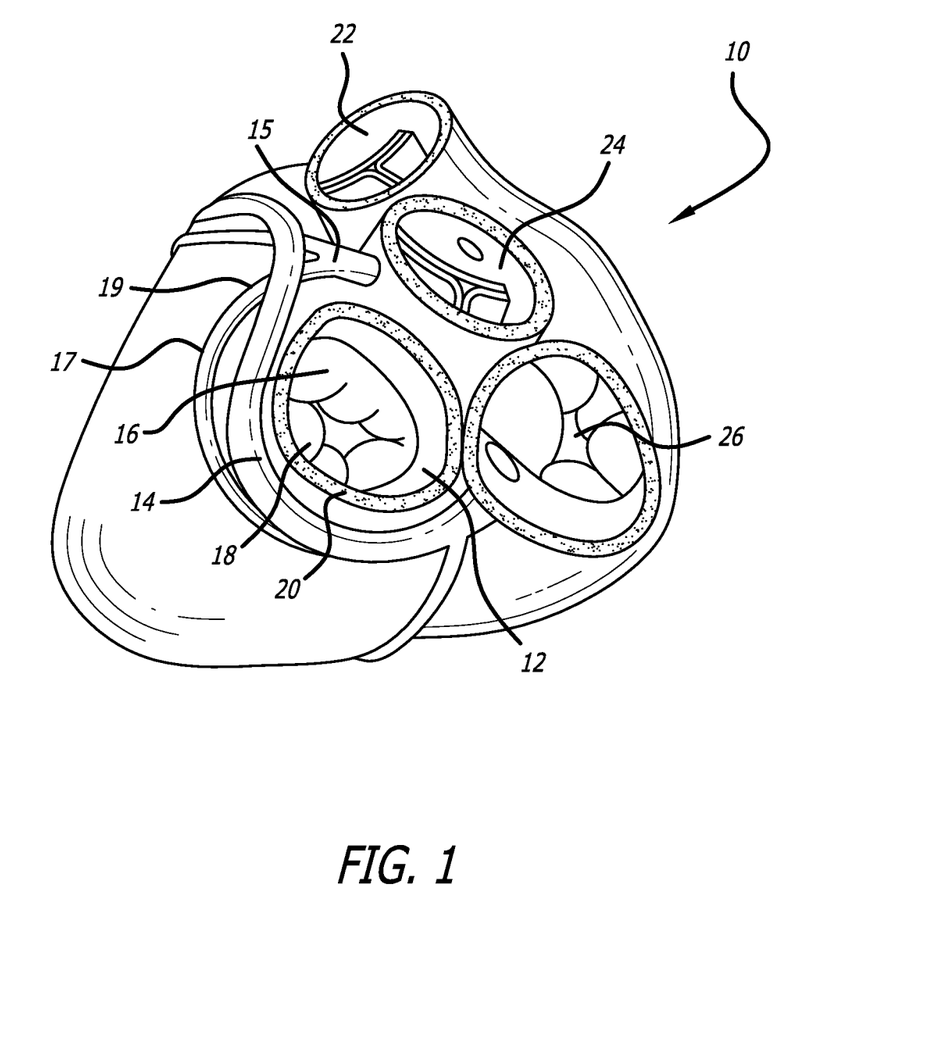
FIG. 1 is a schematic top perspective view through a heart of a human patient, shown in partial cutaway, and showing features that are relevant to the present invention.

With reference to the figures, an embodiment of the invention is described. Referring to FIG. 1, there is shown a superior view of a human heart 10 with the atria removed to expose the mitral valve 12, the coronary sinus 14, the coronary artery 15, and the circumflex artery 17 of the heart 10 to lend a better understanding of the present invention. Also generally shown in FIG. 1 are the pulmonary valve 22, the aortic valve 24, and the tricuspid valve 26 of the heart 10.

The mitral valve 12 includes an anterior leaflet 16, a posterior leaflet 18 and an annulus 20. The annulus encircles the leaflets 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus 14 is part of the venous system of the heart and extends along the atrioventricular (AV) groove between the left atrium and the left ventricle. This places the coronary sinus essentially within the same plane as the mitral valve annulus making the coronary sinus 14 available for placement of the mitral valve therapy device of the present invention therein.

Figure 2:
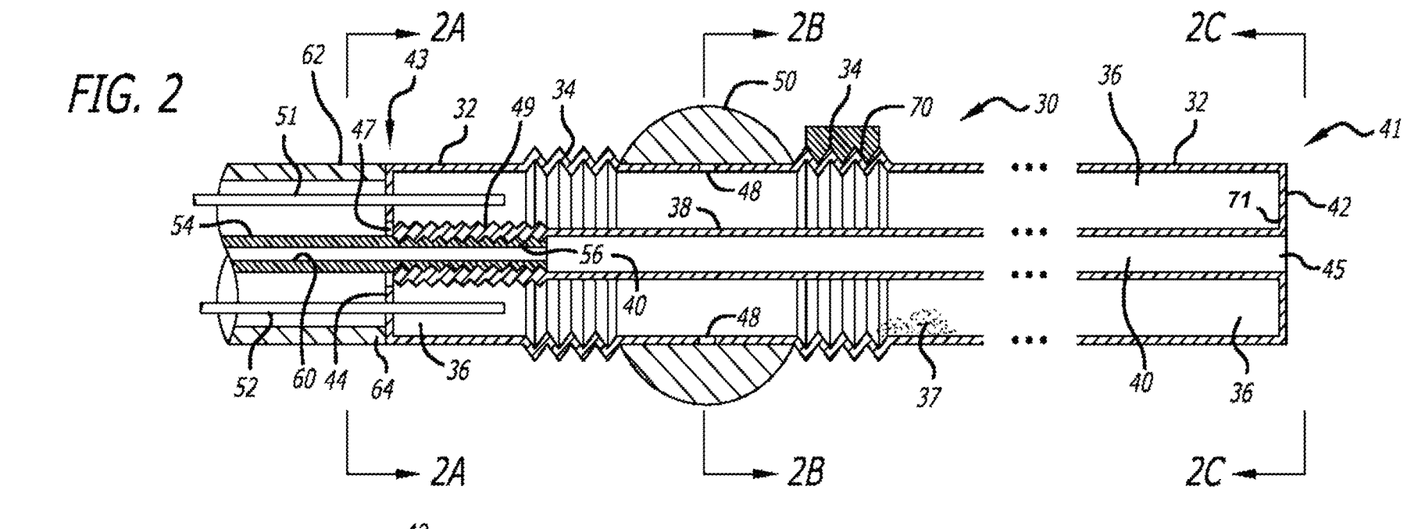
FIG. 2 is a side sectional view a device including features of one embodiment of the invention, the device shown in a first extended condition.

FIG. 2 shows a mitral valve therapy device 30 having features of one embodiment of the present invention. The device is configured to be deliverable into a patient's vasculature on the distal end of a catheter all the way into the coronary sinus, according to known transcatheter delivery techniques.

As is shown in FIG. 2, the device 30 is elongated along an axis and has an initially linear configuration. The device includes a tube 32 which is specially shaped to provide the desired functionality of the invention. In one embodiment, the tube may be made from a polymer which will impart desired flexibility. In another embodiment, an outer wall of the tube is interrupted by a plurality of accordion-like annular shapes which are repeatedly folded and joined together to produce a region that is capable of expanding and contracting in axial length along the tube, and also of allowing the tube to easily bend locally to a small radius of curvature. Each region containing such repeatedly folded regions is referred to herein as a hinge region 34, alternatively, an accordion-like hinge region.

Figure 3:
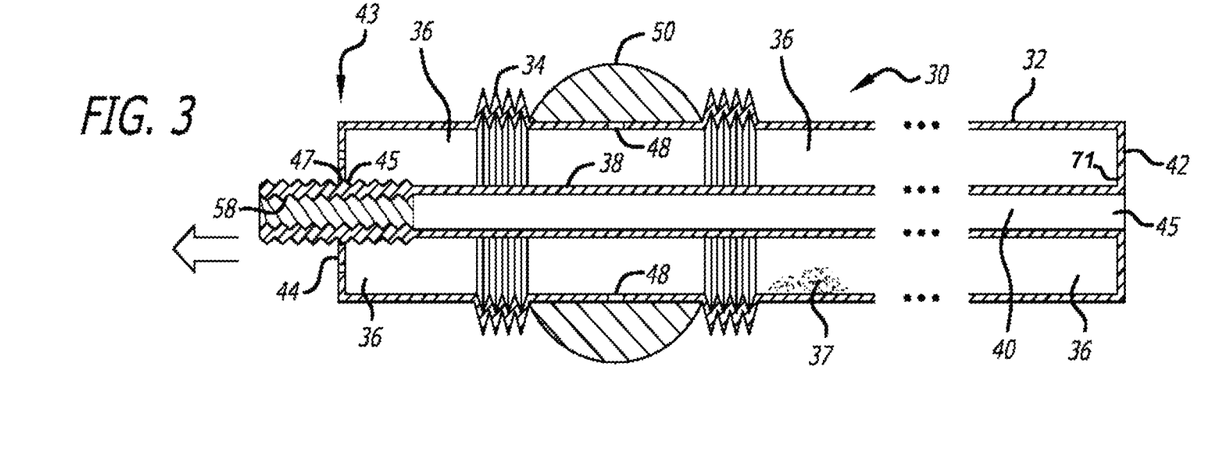
FIG. 3 is a view of the device shown in FIG. 2, the device shown in a second contracted condition.

The hinge regions are designed to permit the tube to have an axially extendable state, shown in FIG. 2, and an axially retracted state, shown in FIG. 3. In the extended state, the tube is longer (for example, having a length D1 shown in FIG. 5) than it is in the retracted state (for example, D2 shown in FIG. 6), and this feature will be utilized to provide advantageous functionality of the invention. The tube 32 defines a first bore 36.

Figure 2A:
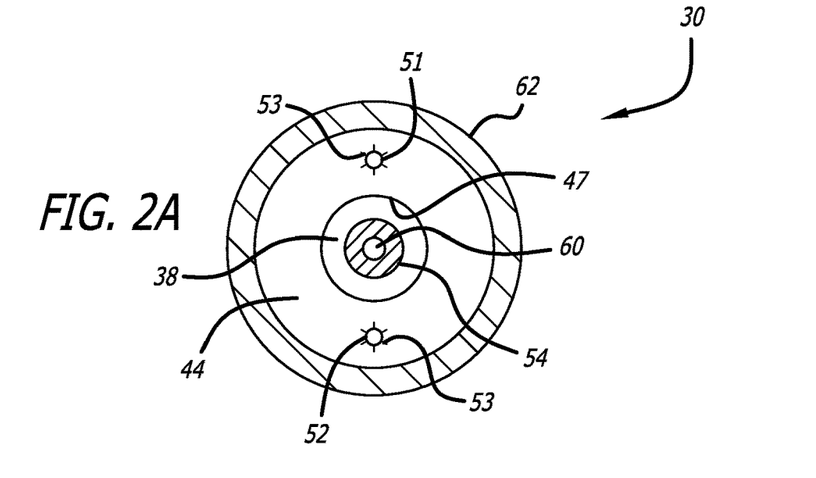
FIG. 2A is a sectional view of the device in FIG. 2, taken substantially along the line A-A.
Figure 2B:
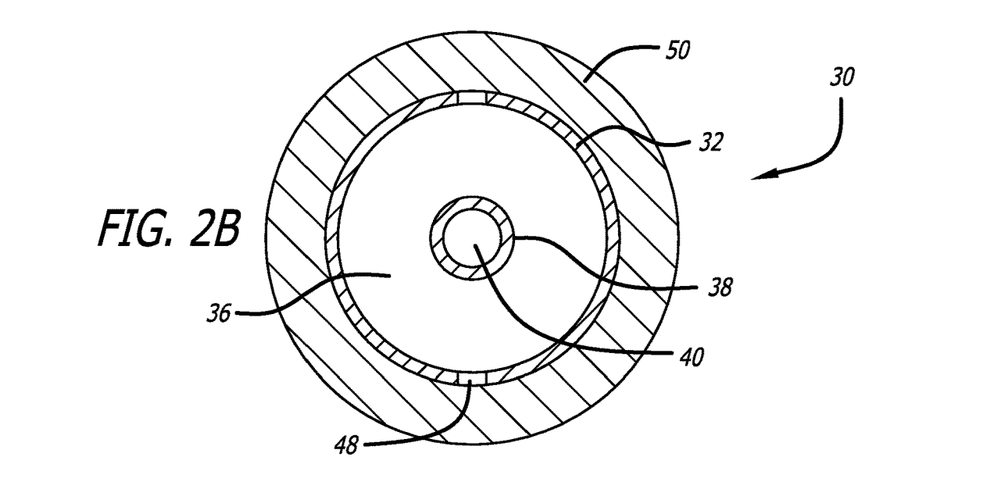
FIG. 2B is a sectional view of the device in FIG. 2, taken substantially along the line B-B.
Figure 2C:
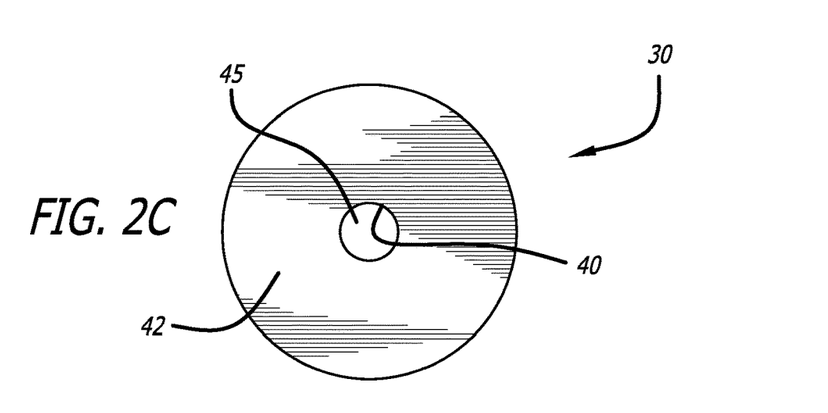
FIG. 2C is an end view of the device in FIG. 2, taken substantially along the line C-C.

As is further shown in FIGS. 2 and 3, an inner member 38 extends along a centerline of the bore 36. The inner member 38 itself has a tubular form and defines a second bore 40. At a distal end 41 of the device 30, the tube 32 is sealed off by a distal flange 42 having an annular form with an opening 45 in the center (FIGS. 2 and 2 c). At a proximal end 43 of the device, the tube 32 is sealed off by a proximal flange 44 having an annular form with an opening 47 in the center. The inner member 38 butts against the distal flange 42 in a sealed connection 71. The inner member 38 passes through the proximal flange 44 in sliding sealed connection 45, so that fluid contained in the outer first bore 36 will be excluded from the inner bore 40. While the connection 45 between inner member 36 and proximal flange 44 is sealed, it is also configured to permit the inner member 38 to slide within the annular opening 47. In some embodiments, the contact between the inner member 38 and the proximal flange is controlled by teeth 49 on an external surface of the inner member. The material of the proximal flange 44 is selected to be sufficiently flexible to act as a pawl against the ratcheting teeth 49 on the inner member, so that after the inner member 38 has been moved a desired amount in the hole 47, its position will be held in a locked condition by the ratchet and pawl effect provided by the teeth and the opening.

In some embodiments, the tube 32 defines small openings 48 in the circumferential wall. These openings are located between the hinge regions 34. Also, positioned on the outer circumferential surface of the tube, between each hinge region 34 and covering the openings 48, a short porous annulus 50 is positioned which is formed in an annular shape to surround the tube. Each annulus is sized so that the outer circumferential surface of the annulus 50 stands radially proud of the hinge regions 34 when the tube is in the retracted state as shown in FIG. 3. These annuli may be formed from a polymer with holes or side vents perforated into the polymer wall by means of forming (mold) or removal (e.g. laser cut) to have the following desirable properties: porosity, suitable for soaking a fluid adhesive that will be ejected from the first bore 36 through the openings 48; stiffness, suitable for forming a connection point between the tube 32 and an inner wall 15 of a coronary sinus 14. The advantage of these features will be elaborated upon below.

Another structural feature of the device 30 is that one or more feeder pipes 51, 52 are positioned to pass through the proximal flange 44. These feeder pipes pass all the way from the volume described by the first bore 36 back to the proximal end of the delivery catheter where they may be controlled by a physician operator. The feeder pipes define inner bores capable of delivering chemical substances to the bore 36. The feeder pipes are also configured to be withdrawn from the proximal flange 44 once their function is complete. The holes in the proximal flange 44 are formed by incising slits 53 in the material of the flange so that they will automatically return to a normally closed condition after the pipes are removed. See FIG. 2A.

Yet a further structural feature of the device 30 in some embodiments is that it is coupled to a delivery element 54. The delivery element extends from the proximal end of the catheter (not shown in the figures) where it is controllable outside the body of the patient using conventional means, and it has an externally threaded distal end 56 which is configured to removably couple with internally threaded proximal end 58 of the inner member 38. In some embodiments, the delivery element may define an internal bore 60 which is suitable for receiving a guidewire 70 (shown in FIG. 4 but not shown in FIGS. 2 and 3).

In embodiments, surrounding the delivery element 54 and the feeder pipes 51, 52 is a hollow cylindrical cover element 62. The cover element extends from the proximal end of the catheter, where it may be manipulated by the physician operator, to the proximal end 43 of the device 30. The distal end 64 of the cover element butts against the proximal end 43 of the tube 32. The cover element 62 does not necessarily couple with the tube, but the interface between the cover element and tube may be provided with mechanical detents that secures the tube 32 against rotation in relation to the cover element 62. This feature is useful in preventing the tube 32 from rotating when the delivery element 54 is rotated at a stage (described below) when it is decoupled from the device 30.

A component of the device which is reflected as element 37 in the drawings, located within the first bore 36, is an adhesive compound 37 that may be introduced into the bore 36 at potentially different stages of the procedure, while still falling within the scope of the invention. The adhesive compound 37 may be a fluid and, as explained in more detail below, may be introduced either before the device 30 is inserted into the vasculature, or it may be inserted only after the device is inserted into the vasculature. Under all embodiments, the adhesive 37 is suitable for forming an adhesive attachment to an inner surface of the coronary sinus. In use, the adhesive compound will be expelled from the openings 48 in the wall of the tube, and will soak into the annuli 50 that cover the openings 48. The saturated annuli 50 will bleed portions of the adhesive compound from an outer surface, which in turn will form a bond with an internal surface 15 (FIG. 6) of the coronary sinus 14. In some embodiments of the invention, the method of performing this outcome is explained in more detail below.

Figure 4:
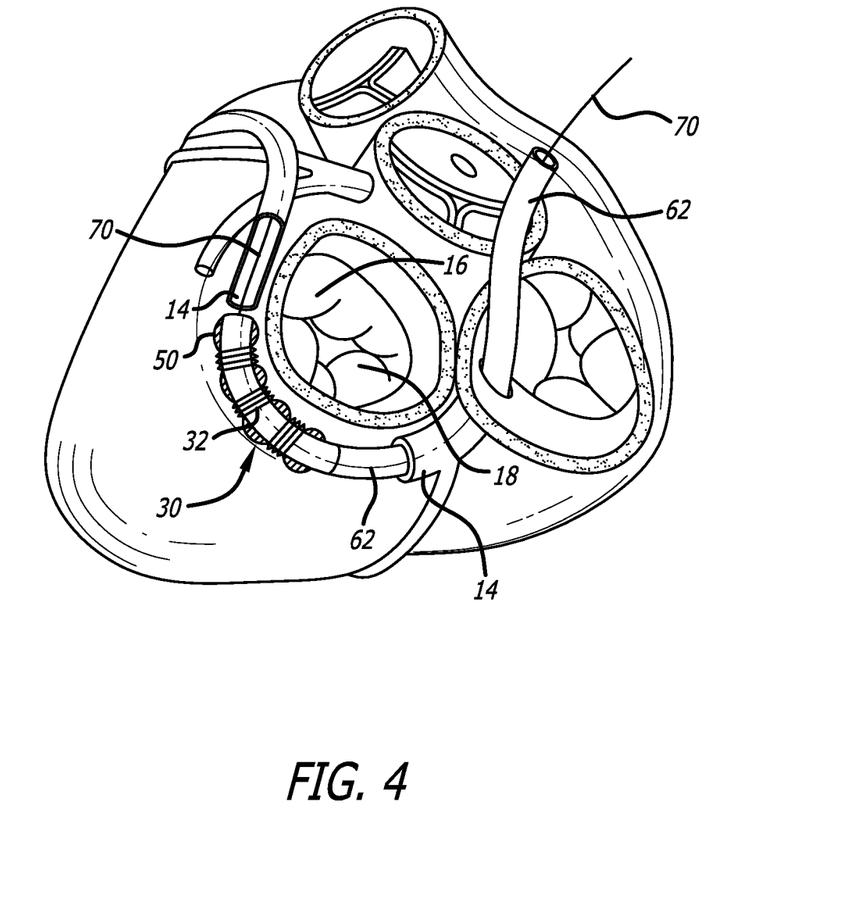
FIG. 4 is a view of the heart of a human patient in FIG. 1, shown in partial cutaway, and showing the insertion of a device such as that in FIG. 2 and FIG. 3.

Turning now to a description of an embodiment of the invention comprising a method of application, wherein the device 30 is applied. FIG. 4 shows the location and manner as to how the device 30 may be implanted in the heart. A guidewire 70 is positioned in the coronary sinus 14 in a known manner, to direct the device to the correct location upon transcatheter delivery. Next, the device 30 is advanced into the coronary sinus of the heart over the guide wire 70. Optionally, the device 30 may be covered in an additional sheath (not shown in the figures) during delivery. The sheath may be withdrawn from the device when the device is in the correct position in the heart. FIG. 4 shows the resulting configuration of the device 30 in relation to the heart 10 after delivery and in an extended condition with length D1. FIG. 4 shows the coronary sinus 14 in partial cutaway in the figure to better reveal the resulting configuration.

As is shown in FIG. 4, the device 30 has been delivered into a curved portion of the coronary sinus. The purpose of the surgeon operator is to attach the device 30 to the interior surface 15 of the coronary sinus 14, and then to shorten the length of the device, thereby to contract the coronary sinus locally, and to force the posterior leaflet 18 towards the anterior leaflet 16 as may be envisaged with reference to FIG. 4. This contraction will have the effect of improving the spacing between the two leaflets to facilitate a more complete closure between them during a left ventricular systole action.

Figure 5:
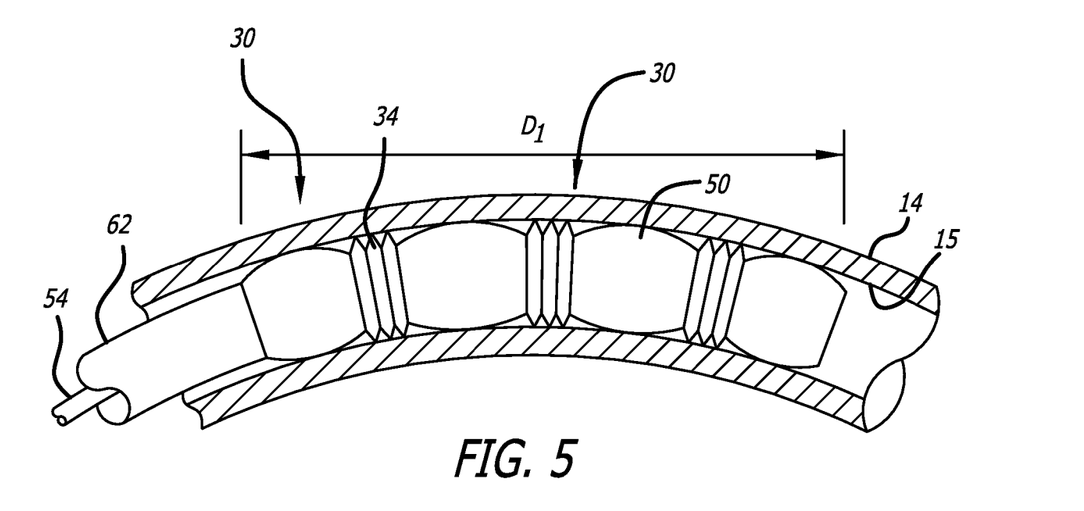
FIG. 5 is a side elevational view of the device in FIG. 2, inserted into a coronary sinus (shown in cutaway) of a human heart, the device shown in the first extended condition.

The contraction may be envisaged with reference to FIGS. 2-6. FIG. 5 shows the device 30 having been inserted into the coronary sinus, as reflected in FIG. 4. At this point, the operator may apply internal pressure to the fluid adhesive in the first bore 36. This end may be accomplished by retracting proximally the delivery element 54 while simultaneously pushing the cover element 62 distally with an equal force. It will be appreciated that this action will cause the distal flange 42, which is attached to the inner member 38 to move slightly proximally towards the proximal flange 44, as shown in FIG. 3. This action results in the volume of the bore 36 to be slightly reduced, and therefore to apply positive pressure to the fluid adhesive in the first bore 36. Another method of applying internal pressure to the fluid adhesive may be to inject a small additional amount of fluid adhesive into the bore by way of feeder pipes 51, 52 which extend from the proximal end of the delivery system into the internal bore via the proximal flange 44. As a result, small quantities of fluid adhesive are expelled out of the openings 48 in the wall of the cylinder 32. These quantities of fluid adhesive soak through the porous annuli 50 surrounding the cylinder 32, and then permeate an exterior surface of the annuli. As a result, the adhesive is able to attach the annuli to an internal wall 15 of the coronary sinus 14 at discrete locations along the length of the cylinder 32 as envisaged by reference to FIG. 5.

Figure 6:
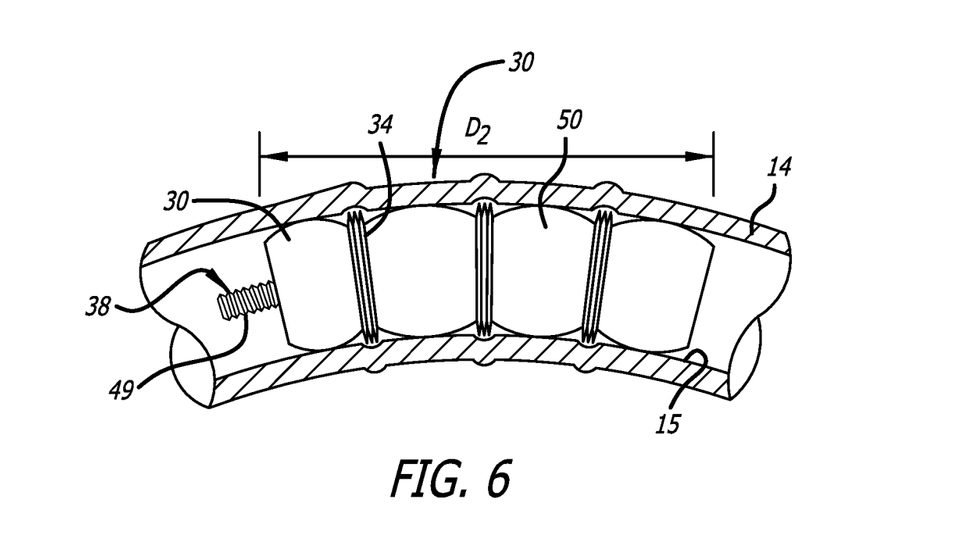
FIG. 6 is a view of the device in FIG. 5, shown attached to an internal wall of the coronary sinus and in the second contracted condition.

At this stage, the procedure is paused, to permit the adhesive to fuse in a permanent state and to robustly attach the annuli 50 to the inner wall 15 of the coronary sinus. Once this is complete, the operator pulls the delivery element 54 proximally by a substantial amount, causing the teeth 49 on the inner member 38 to ratchet through the flexible opening 47 in the proximal flange 44, which acts as a ratchet, so that the inner member remains in a stable position once the force on the inner member is removed; it will be appreciated that at this stage, the seal between the inner member 38 and the proximal flange 44 is closed. When the device is contracted as described, it will be appreciated that the points of attachment between the porous annuli 50 and the tissue of the inner wall 15 are drawn closer together, as shown in FIG. 3. It will be appreciated that this action causes the tissue of the inner wall 15 of the coronary sinus 14 to bunch together, as shown in FIG. 6. Due to the curvature of the coronary sinus 14 this bunching effect in turn causes a force to be applied which urges the posterior leaflet 18 towards the anterior leaflet 16. The posterior leaflet 18 accordingly moves towards the anterior leaflet 16, and coaptation between the leaflets is improved.

In another aspect of the invention, a feature is provided that will cause the device to adopt a configuration in the retracted condition which conforms to a specifically desired bent shape. For example, the nature of the disjunction between the anterior leaflet 16 and posterior leaflet 18 may be such that for an improved coaptation to occur, the posterior leaflet 18 must be lifted vertically to some degree in addition to being moved closer to the anterior leaflet 16. This result may be accomplished in the following manner. With reference to FIG. 2, there is shown how at least one of hinge sections 34 may be locally packed (that is, in this example on an upper portion only) with a stiff adhesive 70 such as epoxy. In the case shown in FIG. 2, adhesive is packed on only the top side as shown, with no adhesive on the lower side. This will have the effect that when the delivery element 54 is pulled proximally and the length of the tube 32 tends to shorten, then instead of the hinge portion 34 that has been packed with adhesive shortening in a uniform manner, the hinge portion will tend to rotate, with the bottom portion of the hinge shortening and the bottom portion of the hinge where the stiff adhesive is packed remaining a constant length. This action will cause the tube to bend upwards at the location of the stiff adhesive 70. Such effect can be usefully deployed by packing stiff adhesive on hinge portions, as desired, so as to provide a predefined shape for the final device. For example, one hinge may be configured to lift upwards, another to bend inwards towards the posterior leaflet 18 so as to enhance the leaflet coapting force. A wide variety of predetermined shapes may be accomplished by fusing the hinge portions at selected locations, as desired.

After altering the shape of the coronary sinus 14 by deploying the device 30, the operator may assess the degree of coaptation of the leaflets using known means. If not satisfied, he may apply more tension to the delivery element 54. Once the operator is satisfied that the device has been shortened to the correct degree, he may take steps to solidify the final shape of the device 30 by curing the fluid adhesive in the first bore 36. To accomplish this step, a curing compound may be pumped into the fluid adhesive along at least one of the feeder pipes 51, 52. In order to stir the fluid adhesive, the fluid pipes may be used in combination, with one pipe introducing a curing agent while the other fluid pipe removes an equal amount of fluid adhesive in order to keep the final pressure in the bore 36 unchanged. In other embodiments, the inner cavity of bore 36 may be primed with a dry element or dry particles of a curing agent that would dissolve and self-mix when fluid adhesive is introduced after the device has been introduced into the desired position. In yet a further alternative embodiment, ultraviolet light may be applied to accelerate curing of the adhesive. In this embodiment, a light tube may be inserted via the internal bore 60 through the delivery catheter from outside the patient.

The warmth of the patient's body will also agitate the molecules of fluid adhesive to mix the curing agent. Within a short while, the fluid adhesive will have hardened under the action of the curing agent. At this point, the operator may rotate the delivery element 54 anticlockwise, thereby removing its threaded distal end 56 from the internally threaded proximal end of the inner member 38. Once the delivery element 54 is removed, the remaining device 30 may appear as shown in FIG. 6. Notably, the inner element 38 has an open bore 40 extending all the way through from proximal end to distal end, and this provides a conduit for blood to flow in, albeit at a reduced flow rate, after the device 30 has been implanted in the coronary sinus 14.

Thus, there is described a novel system and method that addresses needs in the art. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

I claim:

1. A device for adjusting a shape of a coronary sinus in a heart of a patient, the device comprising:
    a flexible tube sized and configured to be positioned in the coronary sinus, the flexible tube having:
        an outer wall extending linearly between a proximal end and a distal end;
        a first bore defined by the outer wall and extending from the proximal end to the distal end;
        a proximal flange attached to the proximal end, the proximal flange defining a proximal opening;
        a distal flange attached to the distal end; and
        an inner member disposed slidingly through the proximal opening and extending through the first bore and connected to the distal flange;
    wherein, the outer wall includes a plurality of accordion-like hinge regions, each hinge region configured to form a bend to adjust a shape of the coronary sinus; and
    wherein the inner member defines a plurality of teeth on an external surface thereof, the plurality of teeth configured to provide a ratchet control for passing slidingly though the proximal opening.

2. The device of claim 1, wherein the inner member defines a second bore.

3. The device of claim 1, wherein the outer wall defines at least one opening disposed between adjacent hinge regions, thereby creating a passage between first bore and a space outside the flexible tube.

4. The device of claim 3, further including at least one porous element attached to the outer wall, and being shaped to cover the at least one opening.

5. The device of claim 4, wherein the at least one porous element has an annular shape.

6. A device for adjusting the shape of a coronary sinus, the device comprising:
    a flexible tube sized and configured to be positioned in the coronary sinus, the flexible tube having:
        an outer wall extending between a proximal end and a distal end;
        a first bore defined by the outer wall and extending from the proximal end to the distal end;
        a proximal flange attached to the proximal end;
        a distal flange attached to the distal end;
    wherein, the first bore is filled with a fluid adhesive;
    wherein the outer wall includes a plurality of hinge regions, and at least one opening defined between two adjacent hinge regions, thereby creating a passage between first bore and a space outside the flexible tube; and
    a porous element attached to the outer wall, the porous element being shaped to cover the at least one opening.

7. The device of claim 6, wherein the proximal flange defines a proximal opening, and an inner member passes slidingly through the proximal opening and extends to, and is connected to, the distal flange.

8. The device of claim 7, wherein the inner member defines a plurality of teeth which act as a ratchet for passing slidingly through the proximal opening, the proximal opening configured to act as a pawl.

9. The device of claim 7, wherein the inner member defines a second bore extending along an entire length of the inner member.

10. The device of claim 6, wherein the porous element is shaped to have an annular shape.

11. A method for adjusting the shape of a coronary sinus in a heart of a patient, comprising:
    inserting a tube into a coronary sinus of the heart, the tube having:
        an outer wall extending linearly between a proximal end and a distal end, the outer wall including a plurality of hinge regions,
        a first bore defined by the outer wall and extending from the proximal end to the distal end,
        a proximal flange attached to the proximal end,
        a distal flange attached to the distal end, at least one opening defined between two adjacent hinge regions, thereby creating a passage between the first bore and a space outside the tube, and a porous element attached to the outer wall, the porous element being shaped to cover the at least one opening;

introducing a fluid adhesive into the bore;

expelling a first amount of the fluid adhesive from the bore through the plurality of openings and, thereby, allowing the tube to become attached to an inner wall of the coronary sinus at a plurality of points adjacent the plurality of openings; and shortening the tube in the direction of the elongate axis, and thereby shortening the coronary sinus.

12. The method of claim 11, further including, adding a curing agent into the bore, thereby causing the fluid adhesive in the bore to harden.

13. The method of claim 11, further including, introducing a source of ultraviolet light into the bore, thereby causing the fluid adhesive in the bore to harden.

14. The method of claim 11, further including bending the tube.

15. The method of claim 14, wherein bending the tube includes applying a longitudinal compression force to the tube in the direction of the elongate axis.

16. The method of claim 11, wherein expelling an amount of fluid adhesive includes reducing a volume of the bore.

17. The method of claim 11, wherein expelling a first amount of fluid adhesive includes adding a second amount of fluid adhesive into the bore.

18. A device for adjusting the shape of a coronary sinus, the device comprising:

a flexible having:

an outer wall extending between a proximal end and a distal end;

a first bore defined within the outer wall and extending from the proximal end to the distal end;

a proximal flange attached to the proximal end;

a distal flange attached to the distal end;

wherein, the first bore is filled with a fluid adhesive;

wherein the outer wall includes a plurality of hinge regions, and at least one opening defined between two adjacent hinge regions, thereby creating a passage between first bore and a space outside the flexible tube; and a porous element attached to the outer wall, the porous element being shaped to cover the at least one opening; and the proximal flange defines a proximal opening, and an inner member passes slidingly through the proximal opening and extends through the first bore and is connected to the distal flange.

* * * * *